United States Patent [19]

Klein et al.

[11] Patent Number: 4,566,805

[45] Date of Patent: Jan. 28, 1986

[54] DEVICE FOR DETERMINING AND CHECKING CONDITION STATE AND OTHER PARAMETERS OF A PRESSURE FLUID

[75] Inventors: Hans-Christof Klein, Hattersheim; Hans Hohmann, Fulda, both of Fed. Rep. of Germany

[73] Assignee: ITT Industries, Inc., New York, N.Y.

[21] Appl. No.: 608,787

[22] Filed: May 10, 1984

[30] Foreign Application Priority Data

May 14, 1983 [DE] Fed. Rep. of Germany ....... 3317638

[51] Int. Cl.$^4$ ............................................. G01N 25/08
[52] U.S. Cl. ..................................... 374/16; 188/1.11
[58] Field of Search ............... 374/16, 21, 141; 73/39; 137/551, 557, 505.11; 251/352; 188/352, 1.11

[56] References Cited

U.S. PATENT DOCUMENTS

| | | | |
|---|---|---|---|
| 2,161,441 | 6/1939 | Vickers | 188/1.11 |
| 3,718,157 | 2/1973 | Siebentritt | 137/551 |
| 3,913,619 | 10/1975 | Aulner et al. | 188/352 |
| 4,164,241 | 8/1979 | Kubo | 188/352 |

FOREIGN PATENT DOCUMENTS 0074415  3/1983  Fed. Rep. of Germany ........ 374/16

Primary Examiner—Charles Frankfort
Assistant Examiner—Patrick R. Scanlon
Attorney, Agent, or Firm—James B. Raden; Donald J. Breh

[57] ABSTRACT

A device for determining or checking the condition, state, or other parameters of a pressure fluid contained in a hydraulic system substantially comprises a body which may be screwed into the wall of a chamber or of a line of the hydraulic system, which at its front face having contact with the pressure fluid has a measuring or testing device, and which at its part accessible from the outside has an electric contact which is in communication with the measuring and testing device via a line passed through a central bore.

8 Claims, 1 Drawing Figure

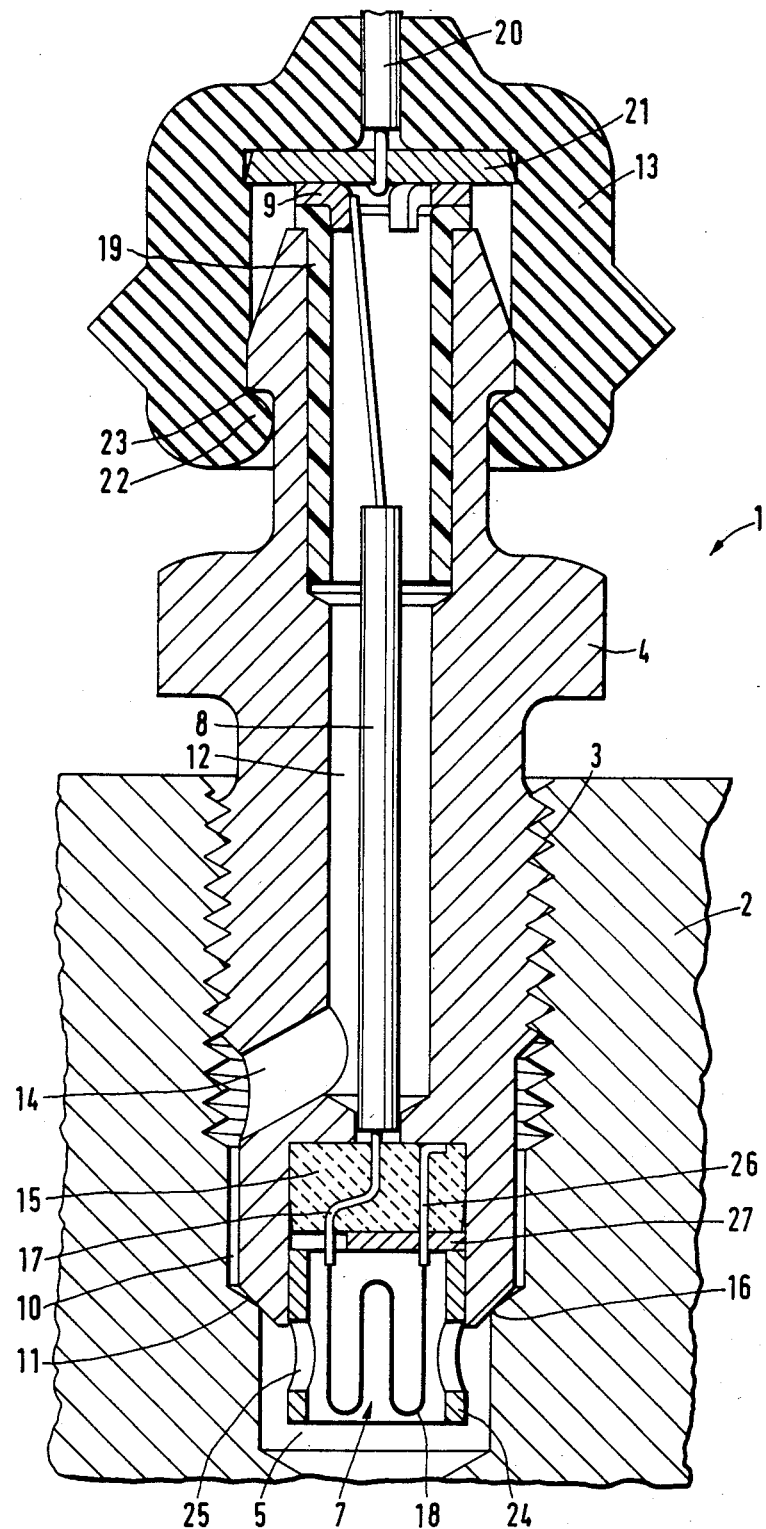

DEVICE FOR DETERMINING AND CHECKING CONDITION STATE AND OTHER PARAMETERS OF A PRESSURE FLUID

BACKGROUND OF THE INVENTION

This invention relates to a device for determining and/or checking the condition, state, and/or other parameters of a pressure fluid contained in a hydraulic system.

Such a device, e.g., is suitable for regular checking of the brake fluid's water content and thus of the brake fluid's effectiveness. As is known, the standard brake fluids are hygroscopic and will thus, amongst other things, permanently absorb moisture from the air via the brake piston seal. Thereby, within a relatively short time, its boiling point will drop from an initial value of 260° to 290° C. down to a value which, with a heavy usaage of the brake, may lead to the formation of vapor bubbles which may be compressed like normal air and will greatly impair the braking action. For the maintenance of a safe brake system it is thus necessary to regularly check the brake fluid. If no testing or measuring device is available this will require a relative frequent exchange of the fluid.

Until now, only relatively expensive and intricate devices are known which allow the brake fluid or samples taken from the brake system to be tested for their water content in the garage. As under favorable circumstances the fluid may age very fast or absorb an excessive amount of moisture, respectively, frequently the boiling point's dropping-down to dangerous values will be realized too late. On the other hand, an exchange of the fluid at very short intervals for the sake of ensuring the operational reliablilty of the brake system is likewise undesirable because of the costs incurred thereby.

It is thus an object of the this invention to provide a device which allows its installation in a hydraulic system and a regular checking of the pressure fluid's condition or state. In particular, the device shall be suitable for building-in into the brake system of automotive vehicles in order to check the boiling point of the brake fluid permanently or, as it were, continuously, e.g. daily, before starting a longer journey, or each time having travelled a predetermined route. A device which would be suitable for such applications would have to operate reliably. It would have to be up to the rough requirements in an automotive vehicle and, above all, it would have to permit its manufacture to be effected with a sufficiently small expenditure.

SUMMARY OF THE INVENTION

It has been found out that this object can be solved in a surprisingly simple and technically very advanced manner by a device of the type mentioned above and substantially comprising a body which may be screwed into the wall of a chamber or a line of the hydraulic system, which at its front face, i.e., at its side facing the pressure fluid, e.g. the brake fluid, is equipped with a measuring or testing device, and which at its part accessible from the outside is provided with an electric contact which is in communication with the measuring or testing device by means of an electric line passed through the inside of the body.

A particularly simple device of the inventive type which allows a manufacture and assembly entailing but small efforts results from the structural uniting, or rather combination, of the device for determining and checking the pressure fluid with a conventional bleeder screw. According to one embodiment of this invention the electric connection of this device to the current supply and to the evaluation circuit may be combined with the mounting of the protecting cap which prevents dirt from entering the vent line.

However, it is also possible to use a conventional plug or clip contact at the part of the device which is accessible from the outside, said contact being independent of the protecting cap and also remaining connected upon the removal of the protecting cap in order to bleed the brake.

BRIEF DESCRIPTION OF THE DRAWING

Further characteristics, advantages, and applications of this invention will become evident from the following description referring to the attached drawing which is the schematically simplified representation of an axial section of a device according to one embodiment of this invention.

DETAILED DESCRIPTION

According to the drawing, the inventive device comprises a by and large rotationally symmetrical body 1 screwed into the the wall 2 of a hydraulic unit by means of the thread 3, the hydraulic unit being e.g. the master cylinder or wheel cylinder of a brake system. To this end, i.e. for placing of the tool, one part 4 of the body 1 has the outside contour of a hexagon head screw.

The screw-in body's 1 front face which, after the insertion into the wall 2, has contact with the pressure fluid or rather plunges into a pressure-fluid-filled chamber 5 or into a pressure fluid line is equipped with the essential part of the invention, the measuring or testing device 7 whose electric contact 8, i.e., an insulated electric cable, is passed through the body 1 outwards, ending there as a contact element arranged in an insulated manner and serving as electric contact 9.

The screw-in body 1 of the particularly advantageous illustrated embodiment is designed as bleeder screw for a chamber filled with hydraulic fluid, e.g. for the working chamber of a brake master cylinder. To this end, in its part screwed into the wall 2 and pointing towards the pressure fluid chamber 5, the body 1 forms an annular chamber 10 communicating with the chamber 5 as long as the body will not be screwed in completely into its seat in the wall. Further, near its front face, the body 1 has a surrounding bevel forming a sealing cone 11. When the body 1 is fully screwed into the chamber 5, the cone will be pressed to abut against a corresponding sealing edge 16 in the wall 2, this sealing the chamber or line 5 containing the pressure fluid relative to the annular chamber 10.

In order to carry out the function of a bleeder screw the body 1 further has a central axial bore 12. Apart from a protecting cap 13 shown in the drawing and not placed on until after the bleeding, said central axial bore 12 is open towards the outside and communicates with the annular chamber 10 via a radial channel 14 inclined towards the inside of the wall 2. Towards the front face of the body 1, the bore 12 is locked by an insulating element 15 through which in this case a naked wire 17 is passed which continues into a wire coil (heating filament 18) arranged at the front face of the body 1 and in this case needed for the measuring and testing device described later on.

The axial vent line of the bore 12, respectively, simultaneously serves for the accommodation of the electric connection line 8 which is advantageous in respect of an easy manufacture. In the bore's 12 side pointing outwards, a short sleeve 19 of insulating material is inserted, preferably pressed in. Through said sleeve 19, the uninsulated end of the cable serving as connection line 8 is passed, said sleeve 19 carrying the contact element 9, in this case a clip placed on the edge of the sleeve 19, and the connection line 8 being solderd on to said clip.

Via the electric contact element 9 the line 8 and hence the measuring and testing device 7 may easily be connected electrically to a cable 20 and thus to a (non-illustrated) current supply and signal evaluation circuit.

To this end, it will be sufficient to press a metal disk 21 against the contact element 9, said metal disk 21 being connected with the cable 20 in an electrically conducting manner. As the contact is large and, if necessary may even be improved by sharp-edged elevations penetrating the corrosion or dirt layers a safe contacting will be achieved in this way. In the represented example of an embodiment of this invention, the required contact pressure will be applied by the protecting cap 13 made of rubber whose inside bead 22 will be slipped over a corresponding edge 23 surrounding the outside surface of the body 1 on the level of the bleeder opening. Due to the inherent elasticity, said inside bead 22 will apply the required contact pressure of the metal disk 21 towards the contact element 9. As such a protecting cap will be needed anyhow in order to prevent the penetration of dirt into the vent line 12, in this way, an electric connection of the measuring and testing device 7 will be provided with a very small expenditure.

In the represented example of an embodiment, the measuring device 7 is accommodated in a protected manner in a sleeve 24 having the design of a short cylinder and having an open front face and openings 25 in its surface area so as to have the wire or heating coil 18 intensely surrounded by the pressure medium. This is important as in this case the wire coil 18 is used as a probe for the determination of the boiling point of the pressure fluid, e.g. of a brake fluid. To this end, via a non-represented electronic circuit, at the time of test, the wire 18 will electrically be heated until, due to the moisture absorbed by the hygroscopic brake fluid, vapor bubbles will form on the surface of the wire which will prevent or delay further heating. By measuring respectively the temperature-responsive specific resistance of the wire 18 or the course of the temperature in dependence on the supplied electric energy it may be determined at which temperature the formation of vapor bubbles will set in or which is the value of the temperature of ebullition of the pressure fluid. If the boiling point of the fluid, in particular of the brake fluid, has dropped to a predetermined value which might endanger the safety of the brake system the evaluation circuit connected to the line 20 will release a signal.

As compared with the feeding line, the wire in the coil 18 has a considerably higher specific resistance so as to ensure that only the wire within the sleeve 24 or the wire coil 18, respectively, yet not the feeding cable, will be heated by the supplied electric energy.

Instead of the wire coil 18 it may also be possible to insert a thermoelement into the sleeve 24 for the determination of the momentary pressure fluid temperature. Thereby a dangerous heating of the pressure fluid may be signaled in time. Sensors of another type, e.g. for measuring the pressure, may likewise be arranged at the front face of the screw-in body 1 and thus be combined with a bleeder screw in the described manner.

In the illustrated embodiment of this invention, the ground connection will be effected via the second wire piece 26 arranged in the insulating element 15, a ceramic socket, via the metallic body 1, and via the screwed joint with the wall 2. Via a metal lamina 27 into which the wire piece 26 is soldered and which is connected with the metallic sleeve 24 it will likewise be ensured that there will be an electrically conducting connection to the ground via the body 1.

As indicated, the device can be used to mount one of many different types of sensors for measuring the condition of the hydraulic pressure fluid including, among others, the two types of boiling point sensors or a pressure sensor, and the drawing is representative of only one: namely a boiling point sensor. Those skilled in the art can readily devise appropriate circuitry, controls, and responsive devices for use with the particular measuring device to be used; and those circuits and controls are not considered to be a part of the present invention.

For bleeding of the hydraulic system one only removes the cap 13 and screws the body 1 out until the sealing cone 11 will lift off from the sealing edge 16. Insofar there is no difference in respect of the known bleeder screws.

We claim:

1. A device for mounting a hydraulic pressure fluid condition measuring device in a hydraulic system of a vehicle comprising:
   a body in the form of a bleeder screw adapted to be screwed into a component of the hydraulic system and including an axial bore defining a vent line, said bleeder screw including means for connecting said hydraulic system to said vent line when partially screwed into said component and for disconnecting said hydraulic system from said vent line when fully screwed into said component;
   a first electrical contact element at an outermost end of said screw, said first contact element electrically insulated from said body and electrically coupled to said measuring device;
   a second electrical contact in the form of a metallic disc within an electrically insulative, protective cap on the outermost end of said screw over said axial bore, said disc in electrical contact with said first contact and electrically coupled to an external lead extending through said cap;
   said screw including means at an end opposite said outermost end thereof for mounting said measuring device in flow communication with said pressure fluid.

2. A device as claimed in claim 1, wherein the body includes a sealing cone at said end opposite said outermost end configured to sealingly engage a corresponding seal edge in the component of the hydraulic system when said screw is fully screwed into said component.

3. A device as claimed in claim 2, wherein said axial bore communicates with the hydraulic system containing the pressure fluid when the screw is partially threaded into said component by way of at least one radially or obliquely extending channel connecting said axial bore to an annular chamber in said component arranged above the sealing cone.

4. A device as claimed in claim 3, wherein the measuring device is electrically connected to the first electric contact by an electrical lead passing through the axial bore.

5. A device as claimed in claim 1, wherein the screw includes a sleeve extending from said end of said screw opposite said outermost end thereof into the hydraulic system containing the pressure fluid, said sleeve surrounds said measuring device, and is provided with openings in flow communication with said pressure fluid.

6. A device as claimed in claim 5, wherein the measuring device is a temperature probe.

7. A device as claimed in claim 1, wherein said measuring device is the type for measuring the boiling point of the hydraulic pressure fluid.

8. A device as claimed in claim 1, wherein said electrically insulative cap engages an edge around said screw proximate said outermost end.

* * * * *